US00PP15735P2

(12) United States Plant Patent
Bol

(10) Patent No.: US PP15,735 P2
(45) Date of Patent: Apr. 26, 2005

(54) ***VERBASCUM* PLANT NAMED 'JACKIE IN PINK'**

(50) Latin Name: ***Verbascum* hybrid**
Varietal Denomination: Jackie in Pink

(76) Inventor: Gerrit H. Bol, Duinzicht 24, Valkenburg, ZH (NL), 2235 BV ( * ) Notice: Subject to any disclaimer, the term of this patent is extended or adjusted under 35 U.S.C. 154(b) by 40 days.

(21) Appl. No.: 10/774,892

(22) Filed: Feb. 9, 2004

(51) Int. Cl.[7] ..... A01H 5/00
(52) U.S. Cl. ..... Plt./263
(58) Field of Search ..... Plt./263

*Primary Examiner*—Kent Bell
*Assistant Examiner*—Louanne Krawczewicz Myers
(74) *Attorney, Agent, or Firm*—Penny J. Aguirre

(57) ABSTRACT

A new cultivar of hybrid *Verbascum,* 'Jackie in Pink', characterized by its pale pink flowers, pubescent grey-green foliage, its compact growth habit, and long blooming habit.

2 Drawing Sheets

Botanical classification: *Verbascum* hybrid.
Cultivar designation: 'Jackie In Pink'.

BACKGROUND OF THE INVENTION

The present invention relates to a new and distinct cultivar of hybrid *Verbascum* plant, botanically known as *Verbascum* 'Jackie in Pink' and will be referred to hereafter by its cultivar name, 'Jackie in Pink'. The new cultivar represents a new Mullein, an herbaceous perennial grown for landscape use.

The inventor discovered the new cultivar, 'Jackie in Pink', in a cultivated growing area at his nursery in Valkenburg, The Netherlands in the summer of 2001. 'Jackie in Pink' originated as a naturally occurring whole plant mutation of *Verbascum* 'Jackie' (unpatented).

Asexual reproduction of the new cultivar was first accomplished by in vitro propagation in Rijswijk, The Netherlands in September of 2002 under the direction of the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Jackie in Pink' from other varieties of *Verbascum* known to the inventor.

1. Pale pink flowers with red-purple centers.
2. Exhibits grey-green foliage with a pronounced pubescent surface imparting a silvery appearance.
3. Reaches a compact height of 40 cm and a spread of about 30 cm at maturity.
4. Long blooming; blooms from June to September in temperate climates.

'Jackie in Pink' differs from the parent plant, 'Jackie', primarily in flower color as the flowers of 'Jackie' are light orange-pink in color. 'Jackie in Pink' can be compared to the cultivar 'Rosie' (U.S. Plant Pat. No. 14,167). Side-by side comparison trials in Valkenburg, The Netherlands, indicated that the flowers of 'Jackie in Pink' are lighter pink in color, the foliage of 'Jackie in Pink' is more pubescent, and the growth habit of 'Jackie in Pink' is more compact (less spreading).

BRIEF DESCRIPTION OF THE DRAWING

The accompanying colored photographs illustrate the overall appearance and distinct characteristics of the new *Verbascum.*

The photograph in FIG. One is a view of a plant of 'Jackie in Pink' in bloom in September as grown in a one-gallon container.

The photograph in FIG. Two is of a close-up view of the flowers of 'Jackie in Pink'.

The colors in the photographs are as close as possible with the photographic and printing technology utilized. The color values cited in the detailed botanical description accurately describe the colors of the new *Verbascum.*

DETAILED BOTANICAL DESCRIPTION OF THE PLANT

The following is a detailed description of 12 month old plants of the new cultivar as grown outdoors in Plymouth, Minn. in one-gallon containers. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

Botanical classification: 'Jackie in Pink' is a cultivar of *Verbascum* of hybrid origin.
Parentage: Naturally occurring whole plant mutation of *Verbascum* 'Jackie' (not-patented).
General description:

*Blooming period.*—June through September in temperate climates.

*Plant habit.*—Herbaceous perennial. Clump-forming, upright flower scapes arise from a rosette of basal foliage. Moderate growth rate.

*Height and spread.*—Reaches about 30 cm in width and about 40 cm in height.

*Hardiness.*—Zone 5–9.

*Culture.*—Grows best in full sun in alkaline, very well-drained soils of low fertility.

*Diseases and pests.*—No susceptibility or resistance to diseases or pests has been observed for 'Jackie in Pink'.

*Root description.*—Fibrous.

Growth and propagation:

*Propagation.*—In vitro propagation is the preferred method, division are also possible.

*Time required for root development.*—8 weeks to fully develop in a 32 cell in soil-less media when grown at 70–80° F. in a greenhouse without supplemental lighting from a rooted plantlet from tissue culture. A 32 cell plug will fully develop in a one gallon container grown outdoors under natural lighting. Fall, winter and spring are preferred for root development.

Stem description:

*Stem size.*—About 1.5 to 3.0 cm in length, 3 to 5 mm in width. Appearance is stemless as foliage is arranged in a basal rosette on short, branchless stems.

*Stem shape.*—Round.

*Stem color.*—N144D.

*Stem surface.*—Villous.

Foliage description:

*Leaf shape.*—Broadly elliptic.

*Leaf division.*—Simple.

*Leaf base.*—Cuneate, mature leaves are extended by a narrow region that is attached to the stem.

*Leaf apex.*—Rounded.

*Leaf venation.*—Pinnate pattern, color N144D on upper and lower surface, raised on lower surface.

*Leaf margins.*—Crenate.

*Leaf attachment.*—Petiolate.

*Leaf arrangement.*—Basal foliage: rosette, flower scapes: alternate.

*Leaf surface.*—Upper and lower: pubescent.

*Leaf color.*—Immature and mature: upper; 138A, lower; 138B.

*Leaf size.*—Up to about 7 cm in length, up to about 3 cm in width.

*Leaf quantity.*—About 10 to 12 per shoot including rosette and scape leaves.

*Petiole length.*—2 cm.

*Petiole width.*—About 3 mm.

*Petiole color.*—N44D.

*Petiole texture.*—Glabrous.

Flower description:

*Inflorescence type.*—Racemes on flower scapes arising from basal foliage.

*Lastingness of inflorescence.*—About 10 days after the first bloom opens. Self-cleaning.

*Flower size.*—About 1.2 to 2 cm in depth and about 3 to 4 cm in diameter.

*Flower fragrance.*—None.

*Flower number.*—About 40 on primary scapes, about 20 on secondary scapes.

*Peduncle size.*—Up to 35 cm in length, 1.5 to 5 mm in width. Secondary branches (1 to 4), up to 25 cm in length, 1.5 to 2.5 mm in width.

*Peduncle shape.*—Round.

*Peduncle color.*—144A.

*Peduncle surface.*—Villous on basal region becoming glabrous towards apex.

*Peduncle internodes.*—5 mm to 2 cm.

*Pedicel bract.*—About 5 mm in length, 1 to 1.5 mm in width, 143A in color.

*Pedicel size.*—About 0.75 to 1 cm in length, about 1 mm in width. Secondary branches (1 to 4 in number), up to 25 cm in length, 1.5 to 2.5 mm in width.

*Pedicel shape.*—Round.

*Pedicel color.*—144A.

*Pedicel surface.*—Glabrous.

*Flower bud size.*—Up to 0.5 cm in length, up to 1 cm in width.

*Flower bud color.*—14D, turning to 70D prior to opening.

*Flower bud shape.*—Globular.

*Flower type.*—Rotate, symmetrical, perfect, outward facing.

*Calyx form.*—Deeply 5 parted, sepals united at base and spreading when flower opens.

*Calyx size.*—About 7 mm in length, 2 mm at base and 1 cm at apex in width when flower opens.

*Calyx color.*—143A.

*Calyx surface.*—Slightly pubescent.

*Sepal number.*—5.

*Sepal size.*—About 7 mm in length, 1.5 mm in width attenuating to apex.

*Sepal apex.*—Acute.

*Sepal margin.*—Entire.

*Sepal surface.*—Slightly pubescent.

*Sepal color.*—143A.

*Corolla features.*—Petals distinct but fused at base to a short tube, 5 mm in length, 144D in color, petals overlap near the proximal region, petals broadly flaring with reflexed edges creating a wavy appearance.

*Petal number.*—5.

*Petal size.*—About 1.5 cm in length, 1.2 cm in width.

*Petal shape.*—Orbicular.

*Petal color.*—Opening: 69B on upper surface and 69C on lower surface, both overlaid with 70D and with markings in center region N79D Fully open: 69D to slightly lighter than 69D on upper and lower surface with markings in center region N79D.

*Petal surface.*—Glabrous.

*Petal margins.*—Entire.

*Petal apex.*—Rounded.

Reproductive organs:

*Gynoecium.*—1 Pistil, 9 mm in length, 1 mm in width; style is 166C in color; stigma flattened, 2-valved, 144B in color, 0.7 mm in length and width; Ovary is superior, 144B in color, 1.2 mm in length and 2 mm in width.

*Androcoecium.*—5 stamens, epipetalous, 2 mm in length and 7 mm in width, filament is 22A in color, covered with showy bristles and N79D in color, pollen is abundant and 25A in color.

*Fruit.*—Septicidal capsule, 3 septum, longitudinally ridged, 4 mm in length, 2.5 mm in width, 146C in color, no seeds observed (empty capsules).

It is claimed:

1. A new and distinct cultivar of *Verbascum* plant named 'Jackie In Pink' as herein illustrated and described.

* * * * *

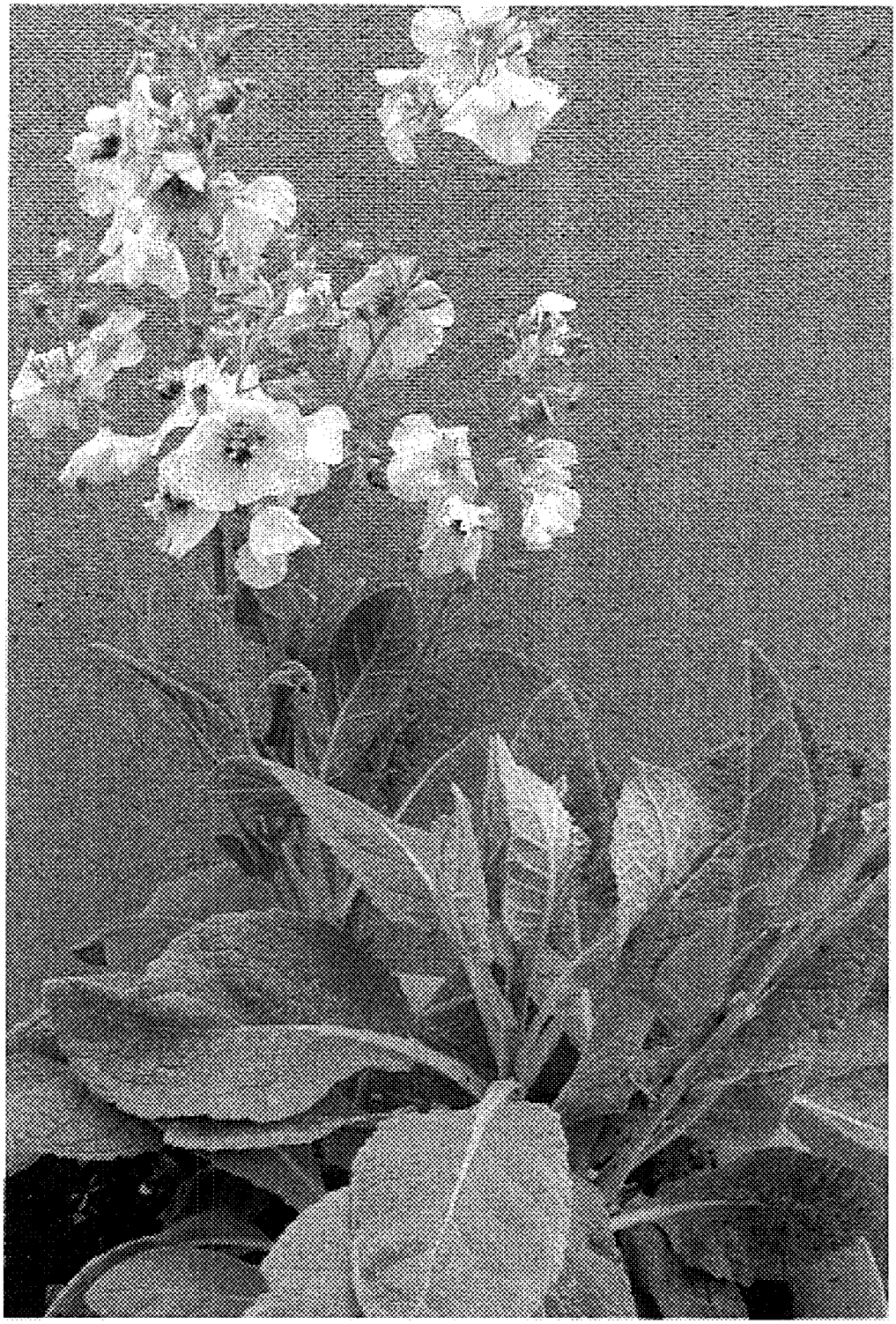
Figure One

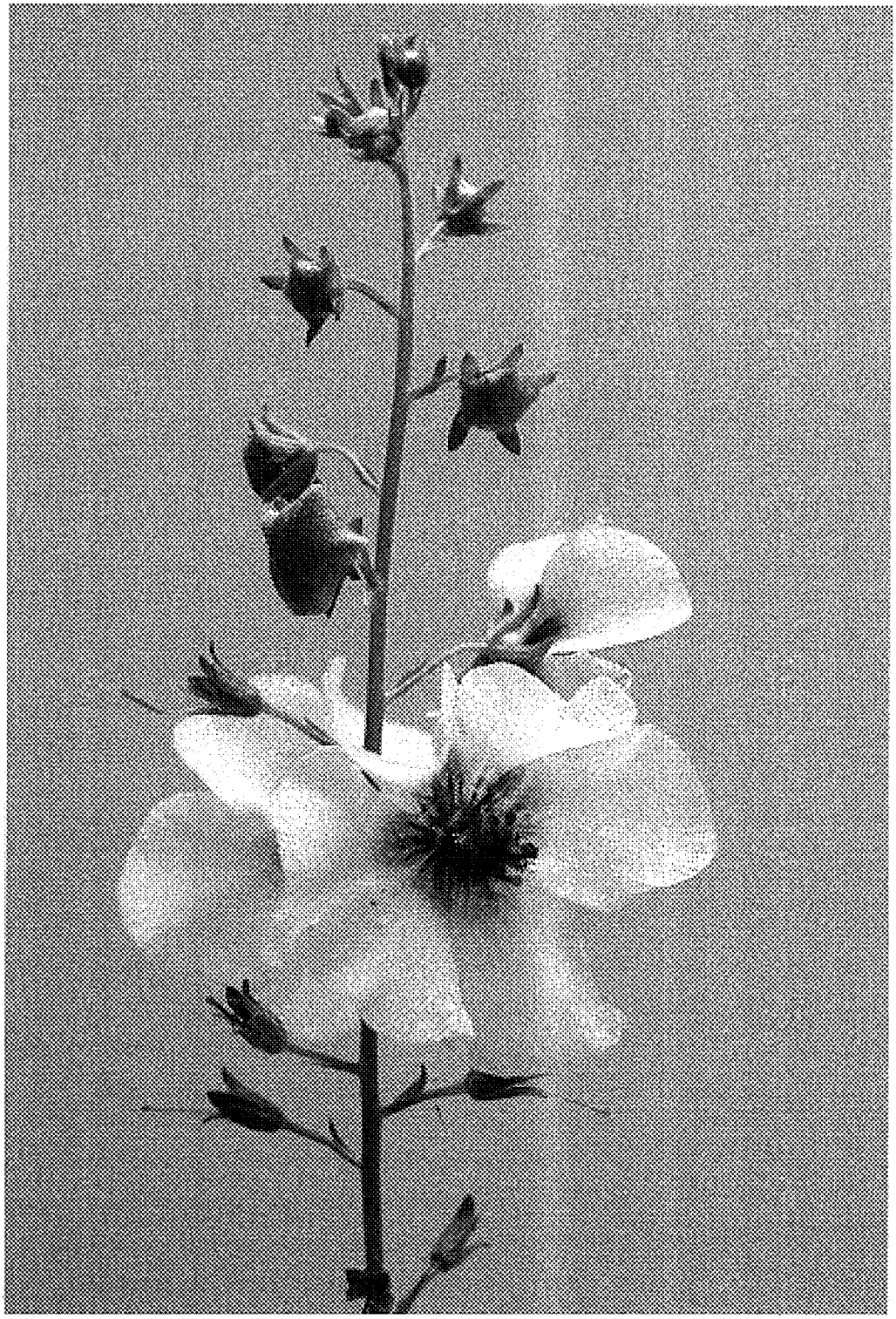
Figure Two